United States Patent
Hickey

(10) Patent No.: US 9,663,802 B2
(45) Date of Patent: May 30, 2017

(54) PROCESSES FOR REMOVING CO-PRODUCED OXYGENATED ORGANICS FROM ANAEROBIC FERMENTATION BROTHS FOR THE BIOCONVERSION OF SYNGAS TO PRODUCT OXYGENATED ORGANIC COMPOUND

(71) Applicant: Coskata, Inc., Warrenville, IL (US)

(72) Inventor: Robert Hickey, Okemos, MI (US)

(73) Assignee: SYNATA BIO, INC., Warrenville, IL (US)

(*) Notice: Subject to any disclaimer, the term of this patent is extended or adjusted under 35 U.S.C. 154(b) by 199 days.

(21) Appl. No.: 14/327,279

(22) Filed: Jul. 9, 2014

(65) Prior Publication Data

US 2016/0010122 A1    Jan. 14, 2016

(51) Int. Cl.
| | |
|---|---|
| C12P 7/54 | (2006.01) |
| C12P 7/06 | (2006.01) |
| C12P 7/16 | (2006.01) |
| C12P 7/52 | (2006.01) |
| C12P 7/04 | (2006.01) |

(52) U.S. Cl.
CPC ........ *C12P 7/54* (2013.01); *C12P 7/04* (2013.01); *C12P 7/065* (2013.01); *C12P 7/16* (2013.01); *C12P 7/52* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 2009/0017512 A1* | 1/2009 | May | ................. | C12M 21/12 435/165 |
| 2009/0305370 A1* | 12/2009 | Grady | ................. | C12P 7/16 435/160 |
| 2011/0097701 A1* | 4/2011 | Hickey | ................. | B01D 53/1425 435/3 |

FOREIGN PATENT DOCUMENTS

WO    WO 2009108503 A1 *  9/2009 ............. C12P 7/065

OTHER PUBLICATIONS

Iwamoto, M. et al. 1999. Effects of nitrate combined with fumarate on methanogenesis, fermentation, and cellulose digestion by mixed ruminal microbes in vitro. Animal Science Journal 70(6): 471-478. specif. pp. 471, 472, 473, 474.*
Glass, C. et al. 1998. Denitrification kinetics of high nitrate concentration water: pH effect on inhibition and nitrite accumulation. Water Research 32(3): 831-839. specif. pp. 831, 832, 835.*

* cited by examiner

*Primary Examiner* — Renee Claytor
*Assistant Examiner* — Sharon M Papciak
(74) *Attorney, Agent, or Firm* — Cardinal Law Group

(57) ABSTRACT

Processes are disclosed for economically and effectively removing co-produced oxygenated organic compound from an anaerobic, aqueous fermentation broth used for the bioconversion of syngas to product oxygenated organic compound. Nitrate anion is added to the broth and the broth is contacted with denitrifying microorganisms that bioconvert the nitrate and organic compounds in the broth to reduced nitrogen compound and carbon dioxide.

15 Claims, 1 Drawing Sheet

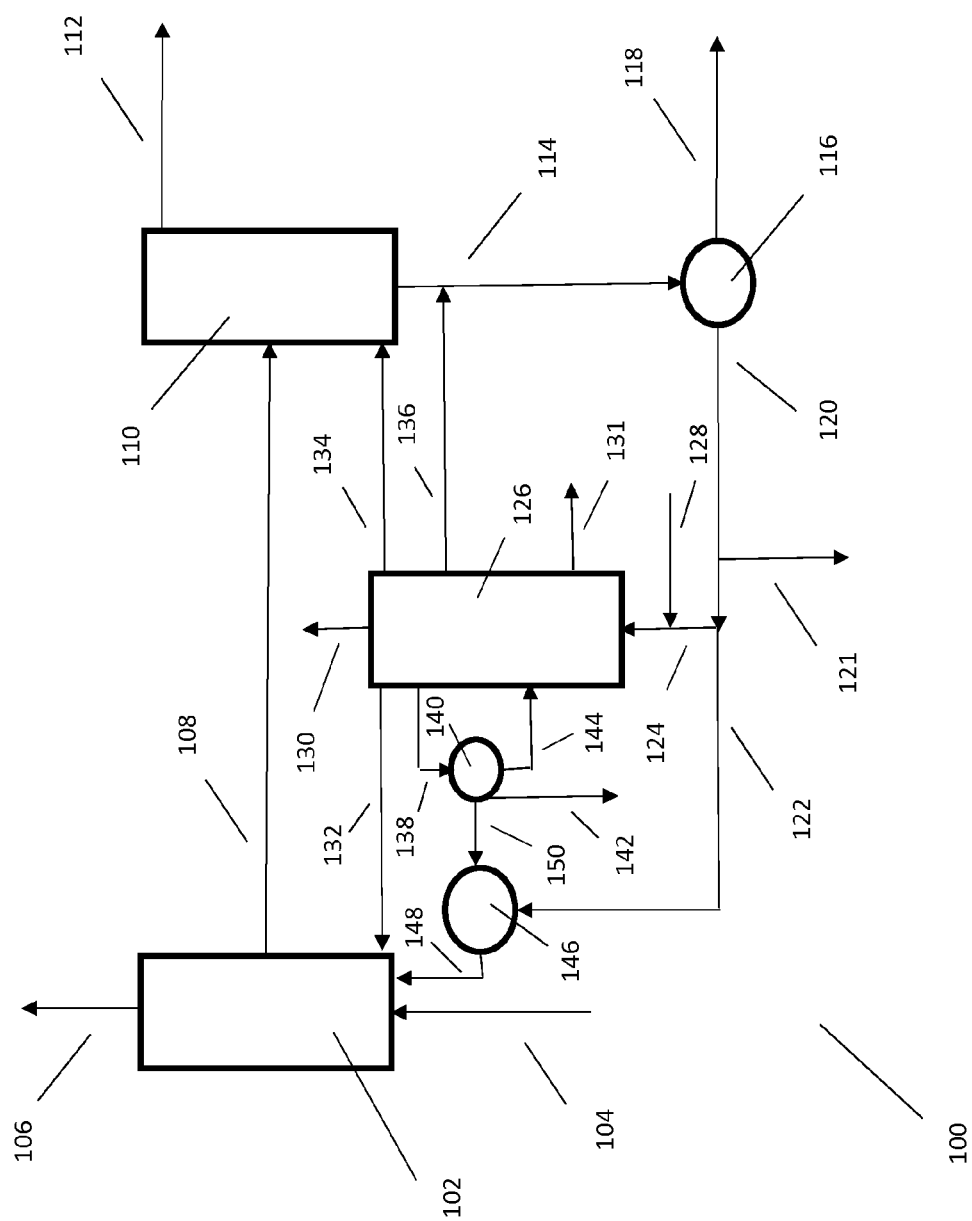

PROCESSES FOR REMOVING CO-PRODUCED OXYGENATED ORGANICS FROM ANAEROBIC FERMENTATION BROTHS FOR THE BIOCONVERSION OF SYNGAS TO PRODUCT OXYGENATED ORGANIC COMPOUND

FIELD OF THE INVENTION

This invention pertains to processes for removing co-produced oxygenated organics from anaerobic aqueous fermentation broths used for the bioconversion of syngas to product oxygenated organic compound, and particularly to such processes using denitrifying microorganisms to remove such co-produced oxygenated organics.

BACKGROUND

Anaerobic fermentations of hydrogen and carbon monoxide involve the contact of a gaseous substrate-containing feed with an aqueous fermentation broth containing microorganisms capable of generating oxygenated organic compounds such as ethanol, acetic acid, propanol and n-butanol. The bioconversion of carbon monoxide results in the production of oxygenated organic compound and carbon dioxide. The conversion of hydrogen involves the consumption of hydrogen and carbon dioxide, and this conversion is sometimes referred to as the $H_2/CO_2$ conversion or, as used herein, the hydrogen conversion.

Typically the substrate gas for carbon monoxide and hydrogen conversions is, or is derived from, a synthesis gas (syngas) from the gasification of carbonaceous materials, from the reforming of natural gas and/or biogas from anaerobic digestion or from off-gas streams of various industrial methods. The gas substrate contains carbon monoxide, hydrogen, and carbon dioxide and usually contains other components such as water vapor, nitrogen, methane, ammonia, hydrogen sulfide and the like. For the sake of convenience, the substrate gas is referred to herein as "syngas" even though it may only contain one of carbon monoxide and hydrogen and may not be derived by the gasification of carbonaceous materials.

These anaerobic fermentation processes are suitable for continuous processes. The syngas is passed into a bioreactor the aqueous fermentation broth for the bioconversion. Off gases can be removed from the bioreactor, and aqueous broth can be withdrawn from the bioreactor for recovery of the oxygenated organic compound at a rate sufficient to maintain steady-state operation. For the anaerobic fermentations to be commercially viable, economies of scale are required. Hence, commercial scale reactors, i.e., those with liquid capacities of at least 1 million, and more often at least about 5, say, 5 to 25, million, liters would be advantageous.

Continuous syngas fermentation processes typically produce co-produced oxygenated organic compounds in addition to the sought, product oxygenated organic compound. The co-produced oxygenated organic compounds can be co-metabolites that are not desired or intermediate metabolites in the bioproduction of the sought, product oxygenated organic compound. Also, co-produced oxygenated organic compounds can be produced by contaminating, or adventitious, microorganisms present in the aqueous fermentation broth. In some instances, these co-produced oxygenated organic compounds may be produced at rates, relative to the production rate of the sought, product oxygenated organic compound, that cause a build-up of the co-produced oxygenated organic compound in the aqueous broth. This build-up of the co-produced oxygenated organic compound is particularly untoward where the co-produced oxygenated organic compound reaches concentration levels that are inhibitory or toxic to the microorganisms used for the syngas fermentation. In some other instances, the co-produced oxygenated organic compound, when at sufficient concentrations, can adversely affect the metabolic pathways of certain microorganisms used for the bioconversion of syngas. For instance, where an alcohol is the sought, product oxygenated organic compound, with some microorganisms, the presence of certain concentrations of free carboxylic acids can induce a product distribution shift in which the microorganisms to generate a higher percentage of carboxylic acids. The exponentially increasing production of the acids leads to an increasing acidity in the fermentation broth causing an eventual loss of the microorganism being able to maintain cell membrane potential and loss of the population of microorganisms.

Although the fermentation broth could be discarded in the event that the concentration of the undesired organic compound becomes excessive, nutrients for the fermentation would also be lost. Additionally, for commercial-scale bioreactors, disposal of the large volume of aqueous broth in a bioreactor can be problematic depending upon the capacity of the waste water treatment system. Since a commercial-scale bioreactor may contain in excess of 1 million liters of aqueous broth, it is likely that the waste water from the bioreactor would have to be slowly discharged to the waste water treatment system to prevent exceeding capacity. Thus, the downtime of the affected bioreactor would be extended, resulting in a further loss of production. The amount of water lost could also be an economic loss.

In some instances, the undesired organic compound may be capable of being selectively removed such as by ion-exchange resins or membrane separations. These approaches may not provide suitable selectivity and are capital intensive yet may only be required sporadically or intermittently. But when needed, these unit operations must be able treat large quantities of fermentation broth in a short period of time. Moreover, they suffer from potential issues with fouling.

Accordingly, processes are sought for the removal of at least one undesired organic compound from an anaerobic fermentation broth that involve low capital expense yet can relatively quickly effect the reduction in concentration of the at least one undesired organic compound while retaining the fermentation broth anaerobic and retaining nutrients. Such desired processes should be capable of treating the large volumes of fermentation broth associated with commercial-scale bioreactors even on a sporadic or intermittent basis.

SUMMARY OF THE INVENTION

By this invention processes are provided for economically and effectively removing one or more co-produced oxygenated organic compounds (referred to herein individually and collectively as the Adverse Component) from an anaerobic, aqueous fermentation broth used for the bioconversion of syngas to product oxygenated organic compound. The processes of this invention can maintain the aqueous fermentation broth as an anaerobic medium and avoid discarding the entire volume of aqueous fermentation broth. Thus, loss of downtime, and lost production of product oxygenated organic compound, and be attenuated. Moreover, the processes of this invention do not require the loss or removal of nutrients from the broth. The processes of this invention are applicable both to addressing catastrophic failures, i.e., where the population of microorganisms in the aqueous fermentation broth has been decimated by the presence of the Adverse Component, and avoidance of catastrophic failure by removal of the Adverse Component prior to reaching untoward concentrations. The Adverse Component is removed by degradation, and the primary degradation products are gaseous and can therefore be readily eliminated from the broth being treated.

The processes in accordance with this invention involve the addition of nitrate anion to the fermentation broth and contacting the broth with denitrifying microorganisms. For purposes herein the term nitrate anion includes anion derived from one or more water-soluble nitrate salts, nitric acid and mixtures thereof. Denitrification occurs under anoxic conditions whereby the nitrate anion is reduced and oxygenated organic compounds (which include the Adverse Component and any product oxygenated organic compound remaining in the broth) are oxidized to carbon dioxide. The nitrate anion is reduced to at least one reduced nitrogen compound, i.e., when the valence of the nitrogen atom is reduced, such as molecular nitrogen, nitrous oxide, nitric oxide, ammonium cation and nitrite anion. In most instances, the reduced nitrogen compound is one or more of molecular nitrogen, nitric oxide and nitrous oxide.

Since the processes of this invention remove the Adverse Component through a fermentation operation, the processes can be practiced without additional undue capital expense. Moreover, the metabolic conditions can be the same or similar to those used for the syngas bioconversion thereby being attractive from an operating expense standpoint. Further, the processes do not necessarily pose the same type of fouling problems associated with the use of membranes or ion exchange resins to remove the Adverse Component.

The processes of this invention can be used to address an unplanned event or can be used on a continuous or intermittent basis to remove Adverse Component co-produced with the product oxygenated organic compound. The processes are suitable for small scale as well as commercial scale facilities for the production of product oxygenated organic compound. Denitrifying microorganisms include those that occur naturally although the broad aspects of this invention include all types of denitrifying microorganisms. The denitrifying microorganisms can be maintained in a bioreactor until needed or can be stored as a freeze-dried or concentrated liquid culture. Thus the processes of this invention can be started-up in a short period of time even from an inoculum to obtain a population of denitrifying microorganisms desired to achieve a sought density of denitrifying activity per unit volume of fermentation broth being treated.

In its broad aspects, the processes of this invention for removing at least one co-produced oxygenated organic compound from an anaerobic, aqueous fermentation broth used for bioconverting syngas to product oxygenated organic compound comprising supplying to the fermentation broth nitrate anion to provide a nitrate-containing broth and contacting the nitrate-containing broth with denitrifying microorganisms under anoxic bioconversion conditions to metabolically produce carbon dioxide and reduced nitrogen compound and an anaerobic fermentation broth having a reduced concentration of said at least one co-produced oxygenated organic compound. Preferably at least a portion, preferably at least about 75, and sometimes at least about 90 or 95, mass percent of the product oxygenated organic compound is removed from the fermentation broth prior to supplying nitrate anion to the fermentation broth (i.e., the implementation of the denitrifying process).

This invention also pertains to continuous processes for the anaerobic bioconversion of a gas substrate comprising carbon monoxide, hydrogen and carbon dioxide in an aqueous broth containing microorganisms suitable for converting said substrate to product oxygenated organic compound, which processes comprise:

a. continuously contacting said gas substrate with said aqueous broth under acidic, anaerobic fermentation conditions to bioconvert gas substrate to oxygenated organic compound and provide a product oxygenated organic compound-containing broth and a depleted gas phase, said anaerobic fermentation conditions also producing an co-produced oxygenated organic compound;

b. continuously withdrawing the depleted gas phase from said aqueous broth;

c. continuously or intermittently withdrawing a portion of said broth for recovery of said product oxygenated organic compound, said withdrawal being sufficient to maintain the product oxygenated organic compound in said broth below a concentration that unduly adversely affects the microorganisms;

d. continuously separating at least one product oxygenated organic compound from the withdrawn portion of said broth to provide at least one fraction rich in said at least one product oxygenated organic compound and a depleted aqueous fraction containing said at least one co-produced oxygenated organic compound;

e. continuously or intermittently adding nitrate anion to at least a portion of the depleted aqueous fraction and thereby provide a nitrate-containing broth and contacting the nitrate-containing broth with denitrifying microorganisms under anoxic bioconversion conditions to metabolically produce carbon dioxide and reduced nitrogen compound and a treated broth having a reduced concentration of said at least one co-produced oxygenated organic compound; and f. using at least a portion of the treated broth to provide an anaerobic aqueous broth for the bioconversion of gas substrate to product oxygenated organic compound.

BRIEF DESCRIPTION OF THE DRAWING

FIG. 1 is a schematic depiction of an apparatus that can be used in the practice of the processes of this invention.

DETAILED DISCUSSION

All patents, published patent applications and articles referenced herein are hereby incorporated by reference in their entirety.

DEFINITIONS

As used herein, the following terms have the meanings set forth below unless otherwise stated or clear from the context of their use.

The use of the terms "a" and "an" is intended to include one or more of the element described.

Oxygenated organic compound means one or more organic compounds containing two to six carbon atoms selected from the group of aliphatic carboxylic acids and salts (lower carboxylates, e.g., acetate anions), alkanols and alkoxide salts, and aldehydes. Often oxygenated organic compound is a mixture of organic compounds produced by the microorganisms contained in the aqueous broth. The sought oxygenated organic compound from the bioconversion of syngas is referred to herein as product oxygenated organic compound or simply oxygenated organic compound unless the context is clear that it is referring to an Adverse Component.

The Adverse Component, i.e., co-produced oxygenated organic compound, is one or more metabolic products from the bioconversion of syngas which may be produced by the microorganism producing the product oxygenated organic compound or an adventitious microorganism. The Adverse Component comprises one or more oxygenated organic compounds other than the product oxygenated organic compound.

A bioreactor assembly is an assembly of one or more vessels suitable to contain aqueous broth and microorganisms for the bioconversion and can contain associated equipment such as injectors, recycle loops, agitators, and the like.

Chemical oxygen demand (COD) is the amount of oxygen required to convert organic carbon in water to carbon dioxide and thus is an indication of the organic compound content of the water. COD is reported as milligrams per liter. One procedure for determining COD is Hach Method 8000, February 2009, Ninth Edition.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

Fossil carbonaceous materials, or fossil fuels, include, but are not limited to, natural gas; petroleum including carbonaceous streams from the refining or other processing of petroleum including, but not limited to, petroleum coke; and lignite and coal.

Aqueous broth, or aqueous fermentation broth, means a liquid water phase which may contain dissolved compounds including, but not limited to hydrogen, carbon monoxide, and carbon dioxide. The broth may, but is not required, to contain microorganisms.

Intermittently means from time to time and may be at regular or irregular time intervals.

Syngas means a gas, regardless of source, containing at least one of hydrogen and carbon monoxide and may, and usually does, contain carbon dioxide.

Overview

The processes of this invention pertain to removing Adverse Component from an aqueous fermentation broth used for the bioconversion of syngas to product oxygenated organic compound, which processes comprise adding nitrate anion to the fermentation broth and using denitrifying microorganisms to degrade the Adverse Component in the course of denitrification.

Syngas Bioconversions

Anaerobic fermentation to produce product oxygenated organic compound uses a substrate (syngas) comprising at least one of (i) carbon monoxide and (ii) carbon dioxide and hydrogen, the latter being for the hydrogen conversion pathway. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier, reformer (steam, autothermal or partial oxidation). Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 65, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing and from industrial processes. These gases may have substantially different compositions than typical syngas, and may be essentially pure hydrogen or essentially pure carbon monoxide. The gas substrate may be obtained directly from gasification or from petroleum and petrochemical processing or industrial processes or may be obtained by blending two or more streams. Also, the gas substrate may be treated to remove or alter the composition including, but not limited to, removing components by chemical or physical sorption, membrane separation, and selective reaction.

The product oxygenated organic compounds produced in the processes of this invention will depend upon the microorganism or combination of microorganisms used for the fermentation and the conditions of the fermentation. Bioconversions of CO and $H_2/CO_2$ to acetic acid, n-butanol, butyric acid, ethanol and other products are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel *Clostridial* Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 described in U.S. Pat. No. 8,143,037.

Mixed cultures of anaerobic microorganisms can also be used for the bioconversions of syngas to product oxygenated organic compounds. See, for instance, U.S. patent application Ser. No. 13/802,916, filed Mar. 14, 2013, entitled Method For Production Of N-Propanol And Other C3-Carbon Containing Products From Syngas By Symbiotic Arrangement Of C1-Fixing And C3-Producing Anaerobic Microorganism Cultures (Toby, et al.); Ser. No. 13/802,930, filed Mar. 14, 2013, entitled Method For Production Of N-Propanol And/Or Ethanol By Fermentation Of Multiple Substrates In A Symbiotic Manner (Enzein, et al.); Ser. No. 13/802,924, filed Mar. 14, 2013, entitled Method For Production Of N-Propanol And Other C3-Containing Products From Syngas Using Membrane Supported Bioreactor (Datta, et al.) and Ser. No. 13/802,905, filed Mar. 14, 2013, entitled Method For Production Of N-Propanol And Other C3-Containing Products From Syngas By Symbiotic Co-Cultures Of Anaerobic Microorganisms (Datta, et al.). C1-fixing microorganisms include, without limitation, homoacetogens such as *Clostridium ljungdahlii*, *Clostridium autoethanogenum*, *Clostridium ragsdalei*, and *Clostridium coskatii*. Additional C1-fixing microorganisms include *Alkalibaculum bacchi*, *Clostridium thermoaceticum*, and *Clostridium aceticum*. Symbiotic C3-producing microorganisms capable of growing on ethanol and/or acetate as their primary carbon source include, but are not limited to, *Pelobacter propionicus*, *Clostridium neopropionicum*, *Clostridium propionicum*, *Desulfobulbus propionicus*, *Syntrophobacter wolinii*, *Syntrophobacter pfennigii*, *Syntrophobacter fumaroxidans*, *Syntrophobacter sulfatireducens*, *Smithella propionica*, *Desulfotomaculum thermobenzoicum* subspecies *thermosymbioticum*, *Pelotomaculum thermopropionicum*, and *Pelotomaculum schinkii*. Pathways for the production of product oxygenated organic compounds having three carbons include, but are not limited to, *Propionibacterium* species (*Propionibacterium acidipropionici*, *Propionibacterium acnes*, *Propionibacterium cyclohexanicum*, *Propionibacterium freudenreichii*, *Propionibacterium freudenreichii shermanii*, *Propionibacterium pentosaecum*) and several other anaerobic bacteria such as *Desulfobulbus propionicus*, *Pectinatus frisingensis*, *Pelobacter propionicus*, *Veillonella*, *Selenomonas*, *Fusobacterium*, *Bacteroides fragile*, *Prevotella ruminicola*, *Megasphaera elsdenii*, *Bacteroides vulgates*, and *Clostridium*, in particular *Clostridium propionicum*.

The aqueous fermentation broth will comprise an aqueous suspension of microorganisms and various media supplements. Suitable microorganisms generally live and grow under anaerobic conditions, meaning that dissolved oxygen is essentially absent from the fermentation broth. The various adjuvants to the aqueous fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

The aqueous broth is maintained under anaerobic fermentation conditions including a suitable temperature, say, between 25° C. and 60° C., frequently in the range of about 30° to 40° C. The conditions of fermentation, including the density of microorganisms and aqueous fermentation broth composition are preferably sufficient to achieve the sought conversion efficiency of hydrogen and carbon monoxide. The pH of the aqueous broth is acidic, often between about 4 and 6.5.

The rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important. Preferably the feed gas is introduced into the bioreactor in the form of microbubbles. Often the microbubbles have diameters in the range of 0.01 to 0.5, preferably 0.02 to 0.3 millimeter.

In some instances, the bioreactor used for the syngas bioconversion may be used for the bioconversion that removes the Adverse Component. In other instances, a separate bioreactor may be used. The bioreactor assembly may comprise one or more bioreactors which may be, with respect to gas flow, in parallel or in series flow. Each bioreactor may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors, including membrane bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

The substrate depleted gas phase egressing from the aqueous fermentation broth will contain a small fraction of the hydrogen and carbon oxides introduced into the bioreactor assembly as the feed gas. Inerts such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, alcohol and the like volatilized from the aqueous fermentation broth.

The bioreactor may have added from time to time or continuously one or more streams of water, nutrients or adjuvants, and microorganisms. A portion of the aqueous fermentation broth is withdrawn from time to time or continuously from the bioreactor for product recovery. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

Adverse Component and Need for Removal

The Adverse Component that is contained in the aqueous fermentation broth for the syngas bioconversion can be from any source, including, but not limited to, an impurity in the feed gas and a metabolic product during the fermentation by the microorganism provided to produce the product oxygenated organic compound or by an adventitious microorganism contained in the fermentation broth.

The removal of the Adverse Component may be prompted by one or more events. One such event is an unplanned event. One type of unplanned event is where normal procedures to avoid the presence of, or limit the concentration of, the Adverse Component in the fermentation broth fail. Another type of unplanned event is where the fermentation broth contains an unexpected microorganism that produces the undesired organic compound. Another type of event is a sporadic or intermittent event such as an anticipated build-up of the Adverse Component which is an inherent co-product.

The Adverse Component can be in a concentration such that the microorganism population for the bioconversion of syngas is substantially killed or is materially, adversely affected, either or both by inhibition and cell death. Alternatively, even if the Adverse Component does not adversely affect the microorganisms for the bioconversion of syngas, its build-up can adversely affect operation. For instance, the build-up may affect the ability to maintain a steady-state operation of a continuous process for making the product oxygenated organic compound.

The time of implementation of the processes of this invention thus can vary according to the cause and effect of the Adverse Component. Thus, the processes may only be used when an unplanned event occurs that adversely affects the population of the microorganisms for bioconverting syngas. Alternatively, the processes may be used intermittently or sporadically to address a build-up of the Adverse Component. This mode of implementation can be beneficial in those instances where higher concentrations of the Adverse Component can have an effect on the metabolic pathways used by the microorganism for the bioconversion of syngas which leads to an accelerated production of the Adverse Component.

The processes of this invention can be used in the presence of viable microorganisms used for the bioconversion of syngas. However, the sustenance of the population of these microorganisms may be problematic in the event that syngas feed is disrupted. Some microorganisms for the conversion of syngas may also bioconvert nitrate anion, but the product of the bioconversion may be ammonium cation rather than nitrogen. In some instances, aqueous fermentation broth has a substantial absence of microorganisms for the bioconversion of syngas. For instance, the microorganisms for the bioconversion of syngas are removed from the aqueous fermentation broth or the broth is denatured prior to being contacted with the denitrifying microorganisms.

The aqueous fermentation broth which is to be treated in accordance with the processes of this invention may contain the product oxygenated organic compound. Since the denitrifying microorganisms can metabolize the product oxygenated organic compound, preferably the product oxygenated organic compound is recovered from the fermentation broth prior to implementing the processes of this invention. Nevertheless, there may be instances where the concentration of the product oxygenated organic compound in the fermentation broth is so low that its recovery may not be practical. Frequently, where the product oxygenated organic compound is recovered, the mole ratio of the product oxygenated organic compound to the Adverse Component in the fermentation broth is less than about 1:1, say, less than about 0.25:1, and sometimes less than about 0.1:1. Where the product oxygenated organic compound is ethanol and the Adverse Component is acetic acid, distillation can reduce this ratio to about 0.01:1 or less.

The processes of this invention can be used in respect of processes for bioconverting syngas to any product oxygenated organic using an aqueous fermentation broth. The preferred product oxygenated organic compounds are alcohols. Where the product oxygenated organic compound is alcohol, typically carboxylic acids are co-produced and, in some instances, these carboxylic acids comprise the Adverse Component. In some instances, other alcohols can also be an Adverse Component, e.g., n-butanol in the production of ethanol or propanol where n-butanol is toxic at a lower concentration to the microorganisms.

Denitrification

Nitrate anion is added to the fermentation broth to be treated by the process of this invention. In the metabolic process of denitrifying, oxygenated organic compound is metabolized, i.e., the nitrate is reduced and the organic compound is oxidized. For instance, where acetic acid is the undesired organic compound, the following represents the overall metabolic reaction:

$$2Na^+ + 2NO_3^- + 1.25CH_3COO^- + 1.25H^+ \rightarrow N_2 + 20H^- + 2.5CO_2 + 2Na^+ + 1.5H_2O.$$

The nitrate anion may be supplied in any convenient form to the fermentation broth which is treated in accordance with this invention. Typically the nitrate anion is supplied as a solid to be dissolved in the aqueous fermentation broth or as a concentrated aqueous solution of dissolved nitrate anion. The amount of nitrate anion required for the denitrification to effect the desired reduction of the undesired organic compound in the aqueous broth may be added initially, or may be added continuously or intermittently as the denitrification proceeds. Often, the peak concentration of nitrate anion is less than about 5, preferably less than about 1, grams per liter of the aqueous fermentation broth, and most often is between about 50 and 1000 milligrams per liter. The lower concentrations of nitrate anion tend to provide a treated fermentation broth that contains little, if any, nitrite anion. Accordingly, the nitrate reduction products will be normally gaseous such as molecular nitrogen, nitrous oxide and nitric oxide, and are exhausted as off-gas.

The amount of nitrate anion added will depend upon the total oxidizable organic content of the organic carbon compounds in the aqueous fermentation broth, and the sought reduction of the Adverse Component. Those skilled in the art of denitrification are readily capable of determining the amounts of nitrate anion required to achieve the sought reduction of undesired organic compound. In one example, the nitrate anion is provided in an amount sufficient to reduce the concentration of one co-produced oxygenated organic compound by at least about 50 percent. In some instances, the processes of this invention will be operated to achieve a certain carbon oxygen demand level in the fermentation broth. In these instances, the COD of the treated aqueous fermentation broth is frequently less than about 5000, preferably less than about 1000, and in some instances less than about 500, milligrams of oxygen per liter.

Often a water-soluble salt or acid of the nitrate anion or mixture thereof is used as the source of nitrate anion. Suitable nitrate salts include, but are not limited to, ammonium, alkali metal (preferably one or more of sodium, potassium and cesium), and alkaline earth (preferably calcium) nitrate. As discussed below, the use of nitrate salts results in the pH of the aqueous medium increasing as the denitrification proceeds. Once a sought pH is obtained, nitric acid may be used as all or a portion of the nitrate anion to maintain a sought pH.

The denitrifying microorganism can be naturally occurring (wild-type) or recombinant, including, but not limited to, genetically modified. As ample types of denitrifying microorganisms are naturally-occurring, these are preferred due to availability, robustness and mitigating any risk of microbial contamination if released to the environment. Examples of denitrifying bacteria include, but are not limited to, *Thiobacillus denitrificans*, *Micrococcus denitrificans*, *Paracoccus denitrificans*, *Spirilum*, *Cornebacteriaum*, *Cytophata*, *Alcaligenes* and *Pseudomonas*.

The denitrifying microorganism can be in a free suspension in the aqueous fermentation broth or may be in the form of a supported biofilm or otherwise immobilized or encapsulated in a solid structure. Support materials may be selected from any hydrophobic or hydrophilic material including, but not limited to, bone char, diatomaceous earth, zeolite, ceramics, clay, wood chips, glass, sand, activated carbon and polymeric materials such as polyethylene, polypropylene, polystyrene, polysulfones, polyacrylates, polymethacrylates, polyesters, nylons, cellulosics, and polyvinyls such as polyvinyl alcohol and polyvinyl chloride. The denitrifying microorganisms may be supplied as an inoculum at the time the process for removing the undesired organic compound needs to be used, e.g., where the denitrifying microorganisms are in a free suspension in the aqueous fermentation broth or are grown on a support during the denitrification process. Alternatively, a prepared solid structure already containing the denitrifying microorganisms on or entrapped or immobilized in the solid structure can be used. Such solid structures are available from Hitachi, Japan; Ecomat, Hayward, Calif.; Lentikats, Czech Republic; and Microvi Biotech, Hayward, Calif.

The processes of this invention may be conducted under any suitable metabolic conditions for the bioconversion of organic compound. In general, the processes are conducted under anoxic conditions such that the treated aqueous fermentation broth can be used for syngas bioconversion to oxygenated organic compound without the need for de-aeration.

Many denitrifying microorganisms are mesophilic and thus are operable within the temperature range used for the bioconversion of syngas. In these instances, the temperature of the aqueous fermentation broth is within the range of about 25° C. to about 40° C. The head pressure during the denitrification is not critical to the broad aspects of this invention, but usually is in the range of between about 50 and 1000 kPa. The pH of the aqueous fermentation broth being treated is preferably greater than about 5.0, and is preferably at least about 5.5. Although the aqueous fermentation broth can be at higher pH levels, e.g., 8 or 9 or more, preferably the pH is maintained below about 7.0 or 7.5 to minimize the adjustment required to reestablish the desired, acidic pH for the syngas bioconversion. The reduction of nitrate salts results in an increase the alkalinity of the aqueous fermentation broth. Hence, initially the pH may be below a desired range for the denitrification, but over time the pH of the aqueous broth will reach that desired range.

Nitric acid can be used as all or a portion of the nitrate anion supplied if the pH becomes higher than desired. Adjuvants and nutrients, including micronutrients, may be added to the aqueous fermentation broth undergoing denitrification. Since the aqueous fermentation broth is from the bioconversion of syngas, at least some nutrients, including micronutrients, typically will already be contained in the broth.

The processes of this invention may be conducted in a batch, semi-continuous or continuous mode. For a batch operation, the duration of the denitrification should be sufficient to achieve the sought reduction in the undesired organic compound. For continuous operations, the residence time of the aqueous fermentation broth in the bioreactor should also be sufficient to achieve the sought reduction in the undesired organic compound.

Any suitable bioreactor assembly may be used in the processes of this invention. The bioreactor assembly can be the bioreactor assembly used for the bioconversion of syngas, or the bioreactor assembly can be separate. The bioreactor assemblies for use in the processes of this invention include, but are not limited to, column reactors; jet loop reactors; stirred tank reactors; fluidized bed reactors; trickle bed reactors; biofilm reactors, including, but not limited to membrane bioreactors; and static mixer reactors including, but not limited to, pipe reactors. Parameters relevant to the selection of the type of bioreactor to be used include the form of the denitrifying microorganism, the volume of aqueous fermentation broth to be treated, and the rate that the denitrification occurs. One or more bioreactors may be used, and when two or more bioreactors are used, they may be in parallel or sequential operation. The bioreactor assembly can, but is not always required to, include heat exchangers; solids separation unit operations such as centrifuges, settling ponds and filters; gas/liquid separation unit operations; pumps; and equipment useful for monitoring and control of the bioreactor assembly.

A separate bioreactor assembly can, if desired, be integrated into the facility for the bioconversion of syngas to oxygenated organic compound. For instance, where the facility contains a distillation assembly, the distillation assembly may be used to remove at least a portion of the product oxygenated organic compound and to denature the aqueous fermentation broth to be treated in accordance with this invention. If the facility uses a centrifuge or other unit operation to separate solids from the fermentation broth, e.g., solids from the microorganisms used for the syngas bioconversion, the treated fermentation broth can be passed to the centrifuge or other unit operation. If the facility uses a sterilization unit operation to treat fermentation broth being recycled to the bioreactor assembly after product oxygenated organic compound recovery, the treated fermentation broth can also be directed to that sterilization unit operation. The broad aspects of the processes of this invention, however, do not require that the treated fermentation broth be sterilized prior to being recycled to the bioreactor assembly.

In preferred aspects of this invention, the treated aqueous fermentation broth need not be de-aerated to be returned to service for the bioconversion of syngas to product oxygenated organic compound. Moreover, since the denitrification products are normally gaseous and evolve from the aqueous fermentation broth as an off gas, the denitrification does not itself lead to any unduly adverse component being generated in the aqueous fermentation broth.

Where the treated aqueous fermentation broth contains denitrifying microorganisms, it is usually the case that the microorganisms are removed from the treated aqueous fermentation broth or the broth denatured such that substantially no viable denitrifying microorganisms are present when the syngas bioconversion is commenced. However, with denitrifying microorganisms that are incapable of surviving under the conditions of the syngas bioconversion, e.g., are not able to tolerate the acidic conditions of the syngas bioconversion or are incapable of surviving in the presence of syngas, removal of the microorganisms may not be essential. The use of such denitrifying microorganisms is particularly useful where the denitrification is conducted in the bioreactor in which the treated aqueous fermentation broth is to be used for the bioconversion of syngas. In some aspects of this invention where the denitrifying microorganisms are not capable of escaping from an immobilizing solid, a unit operation to remove the microorganisms or to denature the broth may not be required.

Where the pH of the aqueous fermentation broth has been allowed to increase during the denitrification, it may be useful to lower the pH prior to reusing the aqueous fermentation broth to convert syngas. Lowering the pH can be accomplished in any suitable manner. Preferably, the concentration of nitrate anion in the treated aqueous fermentation broth is below that which could adversely affect the microorganisms used for the bioconversion of syngas prior to introducing these microorganisms into the broth. Often the nitrate concentration in the treated fermentation broth is less than about 10, and sometimes less than about 5, parts per million by mass per liter of broth. However, some microorganisms for the bioconversion syngas to oxygenated organic compound are able to tolerate presence of nitrate anion, or any adverse effect caused by the nitrate anion, is reversible.

DRAWINGS

A general understanding of the invention and its application may be facilitated by reference to FIG. 1. FIG. 1 is a schematic depiction of an apparatus generally designated as 100 suitable for practicing processes in accordance with this invention. The invention can be operated in either continuous or batch mode. Both are described below. FIG. 1 omits minor equipment such as pumps, compressors, valves, instruments, the exchangers and other devices the placement of which and the operation thereof are well known to those practiced in chemical engineering. FIG. 1 also omits ancillary unit operations. The processes and operation of FIG. 1 will be described in the context of the recovery and production of ethanol. The process is readily adaptable to processes for making other oxygenated organic compounds such as acetic acid, propanol and butanol.

Apparatus contains fermentation reactor 102 which is adapted to hold an aqueous fermentation broth and microorganisms for bioconverting syngas to ethanol. Fermentation reactor 102 is adapted to be operated on a continuous basis. The syngas is provided to bioreactor 102 via line 104. An off gas, which typically contains nitrogen, methane, and unreacted hydrogen, carbon dioxide and carbon monoxide, is withdrawn from bioreactor 102 via line 106. A portion of the aqueous fermentation broth in fermentation reactor 102 is withdrawn via line 108 and is passed to distillation assembly 110. Distillation assembly 110 separates ethanol from the aqueous phase and provides an ethanol rich product which is withdrawn via line 112. The heat in the distillation assembly 110 kills the microorganisms used for the bioconversion of syngas.

A bottoms stream containing solids from the microorganisms and proteins precipitated from solution in an aqueous phase is passed via line 114 to a solids separation unit operation 116, which for purposes of discussion is a centrifuge. The bottoms stream also contains higher boiling organic compounds such as acetates. A solids-rich stream is removed from centrifuge 116 via line 118, and the solids-rich stream can be processed for waste recovery, e.g., in an anaerobic digester. Centrifuge 116 also provides an aqueous stream which exits via line 120 and can be redirected to fermentation reactor 102 via line 122. As shown, a portion of the aqueous stream in line 122 can be withdrawn as an aqueous purge via line 121. Generally, the rate of aqueous purge is at least sufficient to maintain a desired, steady-state ionic balance in the aqueous fermentation broth in fermentation reactor 102. The aqueous purge can be directed to a waste water treatment unit operation.

Line 122 is shown as directing the broth to sterilizing unit operation 146 which for purposes of discussion is a steam heated tank to increase the temperature of the fermentation broth sufficiently to effect sterilization. The sterilized broth is cooled to the desired temperature and returned to fermentation reactor 102 via line 148. Where the temperature of the distillation assembly is sufficient to denature the bottoms stream and the denitrifying microorganisms do not survive under the conditions in the fermentation reactor, sterilizer 146 need not be used.

Line 120 from centrifuge 116 is also capable of directing the aqueous stream to line 124 to be passed to denitrification reactor 126. As shown, nitrate anion (salt and/or nitric acid) can be provided via line 128 to denitrification reactor 126. Denitrification reactor 126 contains denitrifying microorganisms that are either maintained in the reactor as a normal course, when the invention is practiced in continuous mode, or they can be inoculated via line 129 when operated in a batch mode. Off-gases generated by the denitrification exit denitrification reactor 126 via line 130. The batch mode, which is used when a fermentation has reached the point that the adverse compound has reached a level requiring a complete restart of the syngas fermentation, is described first.

In batch mode operation where a restart of the syngas fermentation is required, the broth from fermenter 102 is sent to distillation assembly 110 with the bottoms stream being directed by line 114 to solids separation unit 116. The aqueous stream from solids separation unit 116, which contains a low concentration of solids is passed via line 124 to denitrification reactor 126 and the aqueous stream is accumulated and concurrently treated by adding nitrate through line 128 and a denitrifying inoculum through line 129. Once fermenter 102 is sufficiently empty the treated fermentation broth can be withdrawn from denitrification reactor 126 to refill fermenter 102.

The FIGURE shows several options. The treated fermentation broth can be (i) directly returned to fermenter 102 through line 132 or (ii) sent to solids separation unit 140 via line 138 to remove solids or (iii) can have a portion directed to each path. The solids-containing stream (which contains viable denitrifying microorganisms) can be sent back to reactor 126 via line 144 or passed to a waste treatment facility via line 142. The fermentation broth from which solids have been removed can be passed from solids separation unit 140 via line 150, line 160 and line 148 to fermenter 102 for reuse as the fermentation broth.

In the continuous or semi-continuous mode, the supply rates of both the aqueous stream in line 124, which contains a carbon source for the denitrifying organisms such as an organic acid, and nitrate anion from line 128 are such that the population of denitrifying microorganisms can be maintained. To maintain steady-state operation, a portion of the aqueous fermentation broth in denitrification reactor 126 is removed via line 132. The FIGURE depicts three options for handling the removed broth. In one option, the removed portion of the fermentation broth is passed via line 134 to distillation assembly 110. The broth is denatured in distillation assembly 110. However, depending upon the volume of the broth removed, the heat load for distillation assembly 110 might be unacceptably increased. In a second option, the broth removed is passed via line 136 to line 114. Centrifuge 116 separates the solids and returns fermentation broth to denitrification reactor 126 and/or fermentation reactor 102 via lines 120 and 122. In the third option, the removed broth is passed to line 160 and then to fermenter 102 via line 148. In a fourth option, the removed broth is passed via line 138 to solids separation unit operation 140 (e.g., a centrifuge) to provide a solids-rich stream which exits via line 144 and a solids-depleted stream that can be sent back to fermentation reactor 102 via line 150, line 160 and then line 148. A portion of the solids-rich stream in line 144 returns denitrifying microorganisms to denitrifying reactor 126 via line 145, and the remaining portion is purged via line 142.

When denitrification reactor 126 is used to continuously or intermittently reduce Adverse Component concentration contained in the aqueous stream being returned to fermentation reactor 102, a number of options exist. The process of this invention may be used to prevent an undue build-up of the Adverse Component. In this option, fermentation reactor 102 can continue to operate in a normal mode to produce ethanol. In another option, the syngas feed to fermentation reactor 102 is ceased and the volume of aqueous fermentation broth is decreased or fully removed. The withdrawn fermentation broth is passed to distillation assembly 110 to recover ethanol and is passed to denitrification reactor 126 to bioconvert organic compound. Holding tanks, not depicted, can be used to hold the treated fermentation broth until the desired reduction of volume of fermentation broth has been removed from fermentation reactor 102. In a third option, the syngas feed to fermentation reactor 102 is ceased but the volume of fermentation broth in fermentation reactor 102 is not reduced as treated fermentation broth from fermentation reactor is returned to fermentation reactor 102. Initially, the fermentation broth from fermentation reactor 102 is directed to distillation assembly 110. When the concentration of ethanol in fermentation reactor 102 becomes so diluted that it no longer is efficient to recover ethanol, the fermentation broth withdrawn via line 108 can be directed to line 114 or to denitrification bioreactor 126.

An advantage of the continuous mode operation includes the ability to use denitrification reactor 126 to reduce the load on the wastewater treatment facility in that at least a portion of the liquid purge can be the treated fermentation broth. As shown, line 131 is adapted to remove treated fermentation broth from line 132 for purging. Thus, the volume of fermentation broth passed to denitrification reactor 126 can vary from the rate of the liquid purge to that rate required to effect both the liquid purge and the reduction of Adverse Component.

It is claimed:

1. A process for removing at least one co-produced oxygenated organic compound from an anaerobic, aqueous fermentation broth used for bioconverting syngas to product oxygenated organic compound comprising:
   supplying nitrate anion to the fermentation broth to provide a nitrate-containing broth, wherein the nitrate anion is used in a microbial denitrification process to reduce and remove a co-produced oxygenated organic compound; contacting the nitrate-containing broth
   with denitrifying microorganisms under anoxic bioconversion conditions to metabolically produce carbon dioxide and reduced nitrogen compound and an anaerobic fermentation broth having a reduced concentration of said at least one co-produced oxygenated organic compound; and
   returning at least a portion of the anaerobic fermentation broth having the reduced concentration into the fermentation broth.

2. The process of claim 1 wherein the product oxygenated organic compound comprises at least one alcohol.

3. The process of claim 2 wherein the at least one co-produced oxygenated organic compound comprises lower carboxylate.

4. The process of claim 3 wherein the lower carboxylate comprises acetate anion.

5. The process of claim 1 wherein said nitrate anion is provided in an amount sufficient to reduce the concentration of one co-produced oxygenated organic compound by at least about 50 percent.

6. The process of claim 1 wherein the anaerobic fermentation broth having a reduced concentration of said at least one co-produced oxygenated organic compound is sterilized.

7. The process of claim 1 wherein at least a portion of the product oxygenated organic compound is removed from the fermentation broth prior to the supply of nitrate anion and the contacting with the denitrifying microorganism occur in the bioreactor.

8. The process of claim 1 wherein the aqueous fermentation broth is withdrawn from a bioreactor used for the bioconversion of syngas and is thereafter contacted with the denitrifying microorganisms.

9. The process of claim 8 wherein the concentration of the at least one co-produced oxygenated organic compound in the aqueous fermentation broth used for bioconverting syngas is monitored, and after removal of product oxygenated organic compound, nitrate anion is supplied to the aqueous fermentation broth and the broth is contacted with denitrifying microorganisms under anoxic bioconversion conditions.

10. The process of claim 1 wherein the anoxic bioconversion conditions comprise a pH of at least about 5.5.

11. The process of claim 10 wherein at least a portion of the nitrate anion is supplied by a water-soluble nitrate salt, and the reduction of the nitrate anion from said nitrate salt increases the pH of the nitrate-containing broth.

12. The process of claim 11 further comprising adjusting the pH of the anaerobic fermentation broth having a reduced concentration of said at least one co-produced oxygenated organic compound.

13. The process of claim 1 wherein at least a portion of the anaerobic broth containing a reduced concentration of the at least one co-produced oxygenated organic compound is used as at least a portion of an aqueous fermentation broth for the bioconversion of syngas to at least one product oxygenated organic compound.

14. The process of claim 1 wherein the syngas comprises carbon monoxide, hydrogen and carbon dioxide.

15. The process of claim 1 wherein the anaerobic fermentation broth has a concentration of nitrate anion of less than about 5 parts per million.

* * * * *